(12) United States Patent
Bruneau et al.

(10) Patent No.: US 7,828,825 B2
(45) Date of Patent: Nov. 9, 2010

(54) MULTI-LEVEL MULTI-FUNCTIONAL SPINAL STABILIZATION SYSTEMS AND METHODS

(75) Inventors: Aurelien Bruneau, Memphis, TN (US); Thomas Carls, Memphis, TN (US); Eric C. Lange, Collierville, TN (US); Matthew M. Morrison, Cordova, TN (US); Fred J. Molz, IV, Collierville, TN (US); Jonathan Dewey, Memphis, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 982 days.

(21) Appl. No.: 11/156,739

(22) Filed: Jun. 20, 2005

(65) Prior Publication Data

US 2007/0005063 A1    Jan. 4, 2007

(51) Int. Cl.
*A61B 17/70* (2006.01)
(52) U.S. Cl. .................. 606/260; 606/257; 606/259
(58) Field of Classification Search .................. 606/61, 606/246, 254–260, 263, 278, 279
See application file for complete search history.

(56) References Cited

U.S. PATENT DOCUMENTS

| | | | |
|---|---|---|---|
| 4,361,141 A | 11/1982 | Tanner | |
| 4,771,767 A | 9/1988 | Steffee | |
| 4,854,304 A | 8/1989 | Zielke | |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,474 A | 7/1994 | Lin | |
| 5,336,223 A | 8/1994 | Rogers | |
| 5,403,314 A | 4/1995 | Currier | |
| 5,425,732 A | 6/1995 | Ulrich | |
| 5,486,174 A | 1/1996 | Fournet-Fayard et al. | |
| 5,540,688 A | 7/1996 | Navas | |
| 5,562,660 A | 10/1996 | Grob | |
| 5,575,790 A | 11/1996 | Chen et al. | |
| 5,593,408 A | 1/1997 | Gayet et al. | |
| 5,630,816 A | 5/1997 | Kambin | |
| 5,704,936 A | 1/1998 | Mazel | |
| 6,099,528 A | 8/2000 | Saurat | |
| 6,102,912 A | 8/2000 | Cazin et al. | |
| 6,296,644 B1 | 10/2001 | Saurat et al. | |

(Continued)

FOREIGN PATENT DOCUMENTS

DE    102004011685    *  3/2004    ............... 606/61

(Continued)

OTHER PUBLICATIONS

Gruca, Adam, The Pathogenesis and Treatment of Idiopathic Scoliosis: A Preliminary Report, 1958; 40:570-584, The Journal of Bone and Joint Surgery, United States.

*Primary Examiner*—Eduardo C Robert
*Assistant Examiner*—Tara R Carter

(57) ABSTRACT

Systems and methods for multi-level, multi-functional stabilization of a spinal column segment are provided. The systems include one or more constructs having a motion preserving portion that permits motion of at least a portion of a vertebral level and a motion preventing portion that substantially prevents motion of at least a portion of a second, adjacent vertebral level.

26 Claims, 4 Drawing Sheets

U.S. PATENT DOCUMENTS

| | | | |
|---|---|---|---|
| 6,626,905 B1 * | 9/2003 | Schmiel et al. | 606/279 |
| 6,802,844 B2 | 10/2004 | Ferree | |
| 7,390,329 B2 * | 6/2008 | Westra et al. | 606/151 |
| 2002/0133155 A1 | 9/2002 | Ferree | |
| 2003/0093078 A1 | 5/2003 | Ritland | |
| 2003/0171749 A1 | 9/2003 | Le Couedic et al. | |
| 2004/0002708 A1 | 1/2004 | Ritland | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0143264 A1 | 7/2004 | McAfee | |
| 2004/0215191 A1 | 10/2004 | Kitchen | |
| 2004/0215192 A1 | 10/2004 | Justis et al. | |
| 2004/0267260 A1 | 12/2004 | Mack et al. | |
| 2005/0010220 A1 | 1/2005 | Casutt et al. | |
| 2005/0038432 A1 | 2/2005 | Shaolian et al. | |
| 2005/0065516 A1 * | 3/2005 | Jahng | 606/61 |
| 2005/0085815 A1 * | 4/2005 | Harms et al. | 606/61 |
| 2005/0113927 A1 * | 5/2005 | Malek | 623/17.16 |
| 2005/0124991 A1 * | 6/2005 | Jahng | 606/61 |
| 2005/0131407 A1 | 6/2005 | Sicvol et al. | |
| 2005/0143823 A1 * | 6/2005 | Boyd et al. | 623/17.16 |
| 2005/0171540 A1 * | 8/2005 | Lim et al. | 606/61 |
| 2005/0182401 A1 | 8/2005 | Timm et al. | |
| 2005/0203514 A1 | 9/2005 | Jahng et al. | |
| 2005/0203519 A1 * | 9/2005 | Harms et al. | 606/61 |
| 2005/0261685 A1 | 11/2005 | Fortin et al. | |
| 2005/0277922 A1 | 12/2005 | Trieu et al. | |
| 2005/0288672 A1 | 12/2005 | Ferree | |
| 2006/0009768 A1 | 1/2006 | Ritland | |
| 2006/0036240 A1 | 2/2006 | Colleran et al. | |
| 2006/0052786 A1 * | 3/2006 | Dant et al. | 606/61 |
| 2006/0084982 A1 * | 4/2006 | Kim | 606/61 |
| 2006/0084994 A1 | 4/2006 | Atkinson et al. | |
| 2006/0106381 A1 | 5/2006 | Ferree et al. | |
| 2006/0142760 A1 * | 6/2006 | McDonnell | 606/61 |
| 2006/0149238 A1 | 7/2006 | Sherman et al. | |
| 2006/0189986 A1 * | 8/2006 | Sherman et al. | 606/61 |
| 2006/0260483 A1 | 11/2006 | Hartmann et al. | |
| 2006/0264935 A1 * | 11/2006 | White | 606/61 |

FOREIGN PATENT DOCUMENTS

| | | |
|---|---|---|
| EP | 0 612 507 A1 | 2/1994 |
| EP | 1 488 751 A1 | 12/2004 |
| WO | WO 2005/030066 A1 | 4/2005 |
| WO | WO 2005/039454 A2 | 5/2005 |

* cited by examiner

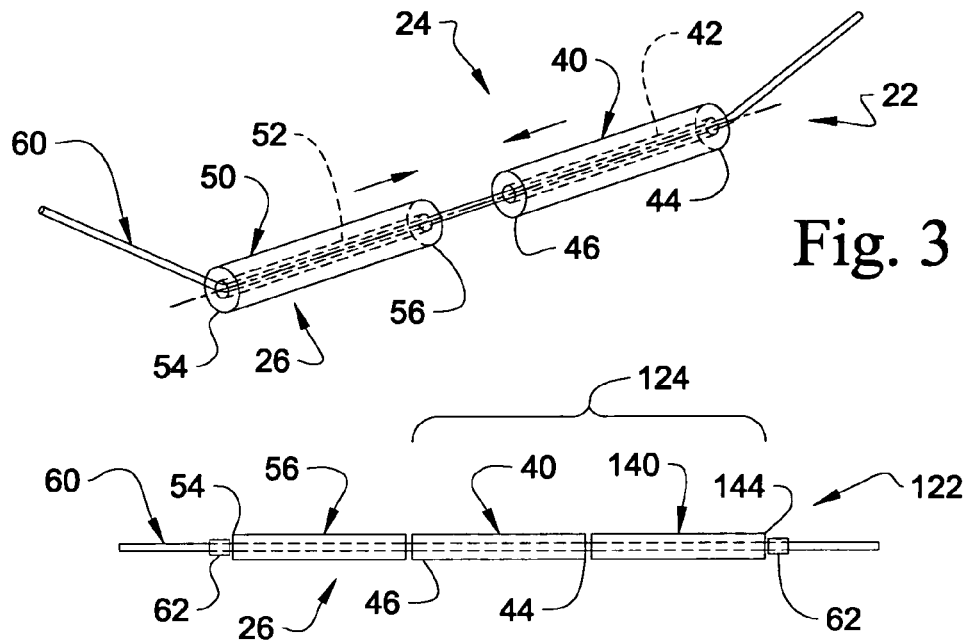
Fig. 3
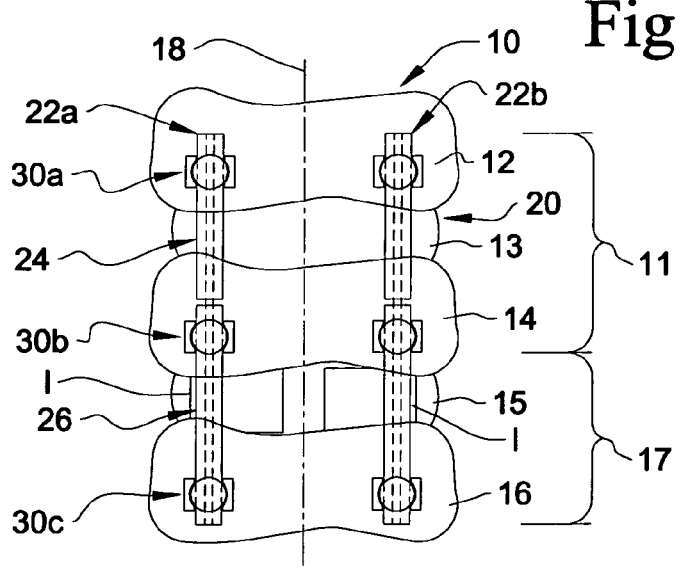
Fig. 4
Fig. 1
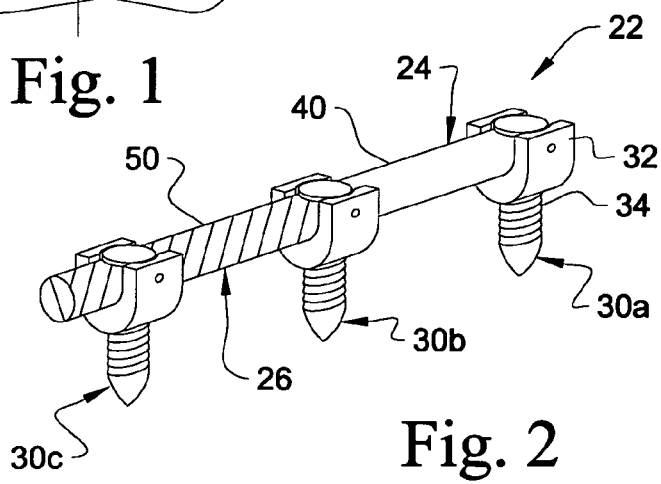
Fig. 2

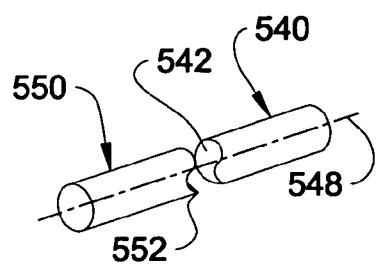 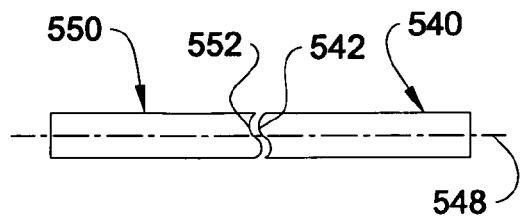
Fig. 9A  Fig. 9B
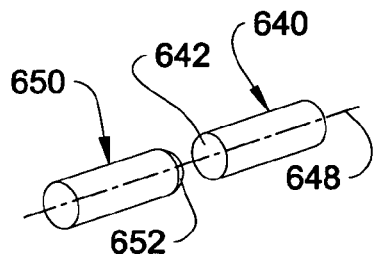 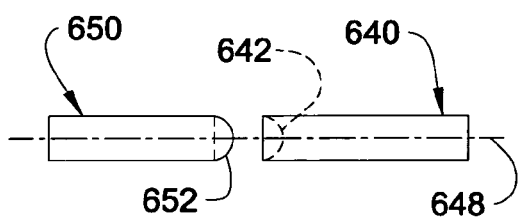
Fig. 10A  Fig. 10B
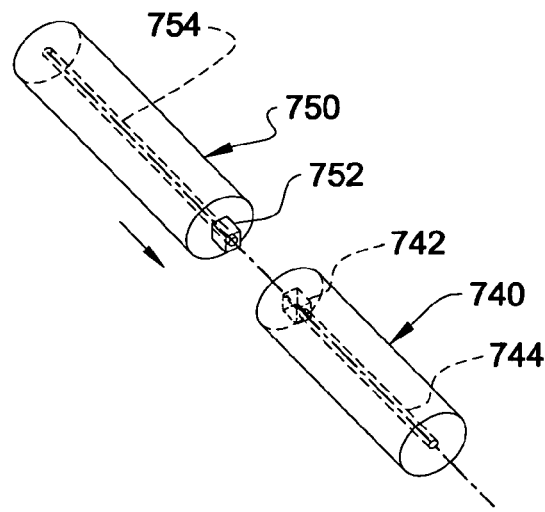
Fig. 11

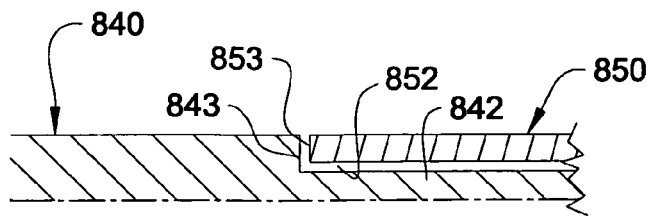
Fig. 12
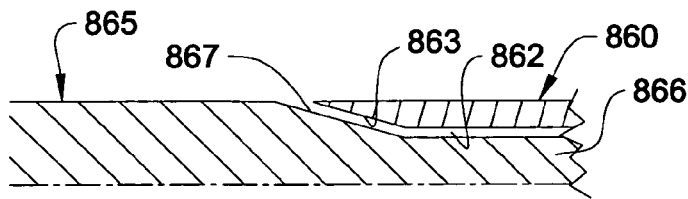
Fig. 13
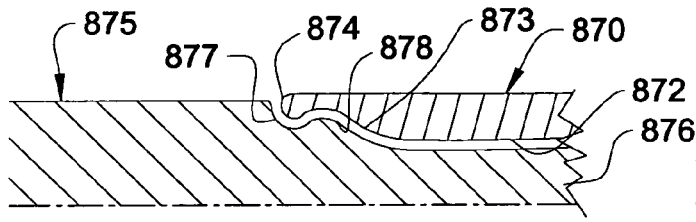
Fig. 14
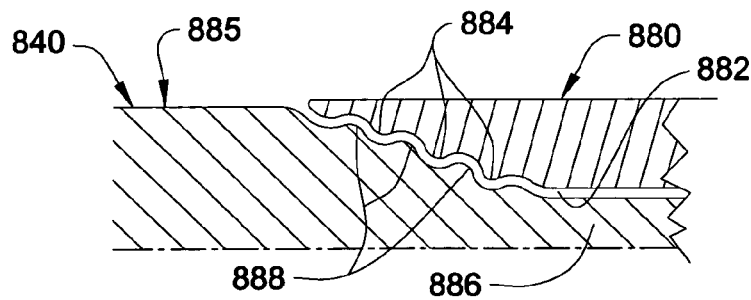
Fig. 15
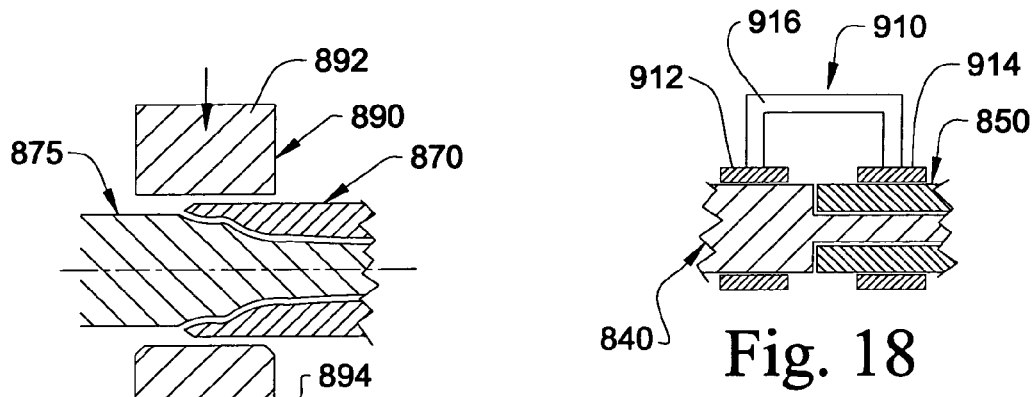
Fig. 16
Fig. 18
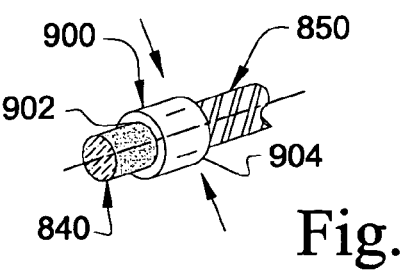
Fig. 17

MULTI-LEVEL MULTI-FUNCTIONAL SPINAL STABILIZATION SYSTEMS AND METHODS

BACKGROUND

Various types of devices and systems have been used to stabilize portions of bones including the spine. Spinal stabilization techniques have employed plating and rods on the posterior, anterior, lateral, postero-lateral and antero-lateral portions of a spinal column segment. Such systems can provide rigid or dynamic fixation of a spinal column segment for the repair of injured or diseased vertebrae, intervertebral discs, and other elements of the spinal column. There remains a need for stabilization systems that are adaptable for various stabilization requirements in a single spinal procedure.

SUMMARY

According to one aspect, a multi-level, multi-functional spinal stabilization system is provided that includes a construct positionable along at least first and second levels of a spinal column. The construct including a motion preserving portion and a motion preventing portion.

In one form, a system is provided where the motion preserving portion includes a first flexible, elongate body flexibly linked with a second substantially rigid, elongate body of the motion preventing portion. The first body includes a length sized to extend between anchors engaged to first and second vertebrae of the first vertebral level, and the second body includes a length sized to extend between anchors engaged to the second vertebra and a third vertebra of the second vertebral level with the first and second bodies in end-to-end engagement with one another.

According to another aspect, a multi-level, multi-functional spinal stabilization system includes a first elongate body having a length sized for positioning between first and second vertebrae of a first vertebral level. The first body is flexible to permit motion of the first vertebral level. A second elongate body includes a length sized for positioning between the second vertebra and a third vertebrae of a second vertebral level adjacent the first vertebral level. The second elongate body is rigid to substantially prevent motion of the second vertebral level. A linking member extends between and flexibly links the first and second bodies with one another in end-to-end engagement.

According to a further aspect, a method for stabilizing at least two levels of a spinal column segment comprises: coupling a first elongate body to a second elongate body with a linking member extending between the first and second bodies; engaging the first elongate body between first and second vertebrae of a first vertebral level, said first body being flexible to permit motion of the first vertebral level; and engaging the second elongate body the second vertebra and a third vertebra of a second vertebral level adjacent the first vertebral level, said second elongate body being rigid to substantially prevent motion of the second vertebral level.

These and other aspects are discussed further below.

BRIEF DESCRIPTION OF THE DRAWINGS

FIG. 1 is an elevation view of a spinal column segment with a multi-level multi-functional stabilization system engaged thereto.

FIG. 2 is a perspective view of a multi-level multi-functional stabilization construct and anchors.

FIG. 3 is a perspective view of a multi-level multi-functional stabilization construct.

FIG. 4 is a perspective view of another embodiment multi-level multi-functional stabilization construct.

FIGS. 9A and 9B are exploded diagrammatic views of one embodiment arrangement between segments of a stabilization construct.

FIGS. 10A and 10B are exploded diagrammatic views of another embodiment arrangement between segments of a stabilization construct.

FIG. 11 is an exploded diagrammatic view of another embodiment arrangement between segments of a stabilization construct.

FIG. 12 is a partial sectional view of another embodiment arrangement between segments of a stabilization construct.

FIG. 13 is a partial sectional view of another embodiment arrangement between segments of a stabilization construct.

FIG. 14 is a partial sectional view of another embodiment arrangement between segments of a stabilization construct.

FIG. 15 is a partial sectional view of another embodiment arrangement between segments of a stabilization construct.

FIG. 16 is the sectional view of the arrangement between segments shown in FIG. 14 with a clamp securing the segments to one another.

FIG. 17 is a perspective view showing a circumferential crimp securing segments of a stabilization construct.

FIG. 18 is a sectional view of another embodiment arrangement between segments of a stabilization construct and a bracket securing the segments to one another.

DESCRIPTION OF THE ILLUSTRATED EMBODIMENTS

Figure 7:
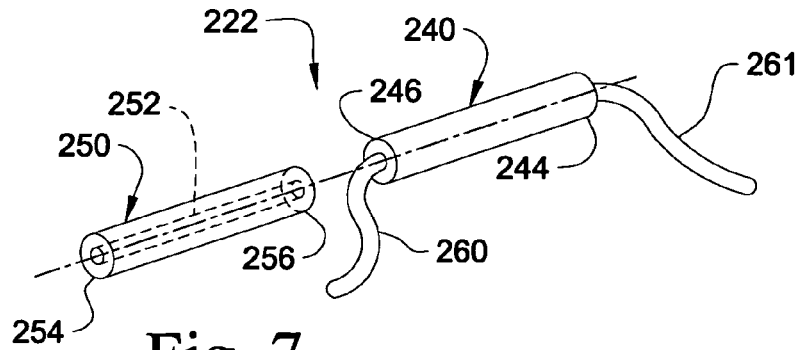
FIG. 7 is an exploded perspective view of another embodiment multi-level multi-functional stabilization construct.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

Multi-level and multi-functional stabilization systems are provided for attachment to a spinal column segment. The systems include one or more stabilization constructs positionable along the at least two levels of the spinal column and engageable thereto to provide multi-functional stabilization. The stabilization construct includes a motion preventing segment engageable along at least one level of the spinal column to effectively immobilize the at least one level and a motion preserving segment engageable along at least one level of the spinal column adjacent the at least one immobilized level to provide dynamic stabilization.

The system can be engaged posteriorly, anteriorly, antero-laterally, laterally, or in any other position to the spinal column segment. Combinations of approaches and stabilization are also contemplated such as, for example, anterior and posterior stabilization construct. The systems can employed with fusion of one or more vertebral levels with bone graft alone or in combination with one or more fusion devices in a disc space between vertebrae. Furthermore, the systems can be employed with artificial discs or motion preserving devices in one or more vertebral levels either alone or in combination with fusion of one or more other vertebral levels. The fusion devices and artificial discs can be positioned through the same approach or through differing approaches than that taken for placement of the stabilization system.

Referring now to FIG. 1, there is shown one embodiment multi-level multi-functional stabilization system 20 secured to a spinal column segment 10. System 20 includes first and second stabilization constructs 22a, 22b engaged along opposite sides of the spinal column segment 10. Other embodiments contemplate systems employing one construct or more than two constructs. Constructs 22a and 22b are collectively and individually referred to as construct 22 herein.

Construct 22 is adapted to extend along at least two vertebral levels. A first vertebral level 11 includes a first vertebra 12, an intermediate vertebra 14 and a disc space 13 therebetween. The second vertebral level 17 includes intermediate vertebra 14 and a second vertebra 16 with a disc space 15 therebetween. A first construct segment 24 extends the first vertebral level 11, and a second construct segment 26 extends along second vertebral level 17. Other embodiments contemplate that either or both of first and second segments 24, 26 extend along multiple vertebral levels. It is further contemplated that the first vertebral level 11 can be located cephaladly or caudally of second vertebral level 17.

In one form, the multi-level multi-functional construct 22 includes a motion preserving portion defined by first construct segment 24 and a fixation portion defined by second construct segment 26. The motion preserving portion at least partially maintains the movement capability of first vertebral level 11 while the fixation portion substantially prevents movement of at least a portion of second vertebral level 17. In one procedure, one or more implant I can be positioned in disc space 15 of second vertebral level 17. Implants I can be fusion devices designed to promote or facilitate bony fusion between vertebrae 14, 16 while second construct segment 26 prevents or resists relative movement between vertebrae 14, 16 to facilitate bone growth and formation of bony continuity between vertebra 14, 16. First construct segment 24 simultaneously provides dynamic stabilization of first vertebral level 11, preserving at least partially the motion capabilities of first vertebral level 11 while sharing load carrying to the anchors of the system 20. Construct segment 24 can provide treatment, revision or prevent degeneration of one or more vertebral levels adjacent one or more vertebral levels to be fused.

As further shown in FIG. 2, system 20 includes a number of anchors 30 engageable to vertebrae along the spinal column segment to couple construct segments 24, 26 to the vertebra. In the illustrated embodiment of FIG. 1, anchor 30a is engaged to vertebra 12, anchor 30b is engaged to vertebra 14 and anchor 30c is engaged to vertebra 16. Each of the anchors 30 can include a receiving portion 32 and an anchoring portion 34. Anchoring portion 34 may include any suitable form for engaging one or more of the vertebrae. Examples of contemplated forms for anchoring portion 34 include bone screws either multi-axial or uni-axial in form, hooks, staples, tethers, interbody devices, artificial discs, fusion devices, and cables. The anchoring portions for any two or more of the anchors may be of the same form or of different forms. Receiving portion 32 may be in the form of a post, saddle, clamp, top-loading connector, side-loading connector, bottom-loading connector, or any other suitable device for engaging construct 22 with the respective anchor portion 34. Receiving portions 32 may be of the same form for each of the anchors 30, or of differing forms.

First construct segment 24 includes a motion preserving member 40 engageable with anchor 30a, and second construct segment 26 includes a motion preventing member 50 engageable with anchors 30b, 30c. It should be understood that motion preserving member 40 may be engaged with multiple anchors anchored to one or both of vertebrae 12, 14 or one or more other vertebrae. Motion preventing member 50 may be engaged with more than one anchor to either of vertebrae 14, 16. Motion preventing member 50 may also be engaged to one or more other vertebrae. In FIG. 2, motion preventing member 50 and motion preserving member 40 are elongate rod-like structures positionable against one another in end-to-end fashion. Other embodiments contemplate other arrangements, as discussed further below.

One embodiment is shown in FIG. 3. Construct 22 includes motion preserving member 40, motion preventing member 50, and a linking member 60 extending therebetween. Motion preserving member 40 includes a passage 42 extending between outer end 44 and intermediate end 46. Motion preventing member 50 includes a passage 52 extending between an outer end 54 and an intermediate end 56. Linking member 60 extends through passages 42, 52 and couples motion preserving member 40 with motion preventing member 50. Members 40, 50 can be moved toward one another along linking member 60 until intermediate ends 46, 56 are adjacent one another or are in abutting contact with one another.

In one embodiment, linking member 60 is a flexible cord threaded or positioned through passages 42, 52. One of the outer ends 44, 54 can be crimped to secure linking member in the respective passage 42, 52. Linking member 60 is then pulled tight, and the other outer end 44, 54 is crimped to secure linking member 60 with the respective member 40, 50. Linking member 60 maintains members 40, 50 in contact with one another at intermediate ends 46, 56 to facilitate load sharing therebetween.

In addition to or in lieu of crimping of the members 40, 50, various mechanisms are contemplated for securing members 40, 50 in position about linking member 60. For example, crimps or other members may be secured about linking member 60 adjacent ends 44, 54 to maintain intermediate ends 46, 56 in contact with one another. In another example, linking member can be knotted or enlarged adjacent respective ones of the other ends 44, 54, or 144 such as shown and designated at 62 in FIG. 4. In further examples, a fastener or other coupling device can extend between and engage linking member 60 with the respective motion preserving and motion preventing members 40, 50. In still a further example, anchors 30 can a set screw or other engaging device crimp or otherwise secure motion preserving and motion preventing members 40, 50 in position relative to linking member 60 when engaged with construct 22.

Motion preserving and motion preventing members 40, 50 are shown with circular cross-sections. Other embodiments contemplate other cross-sectional shapes, including polygonal, non-circular, rounded and irregular shapes. It is further contemplated that the cross-sectional properties, shapes and/or sizes may vary along the length of the members 40, 50. Passages 42, 52 can be aligned centrally through members 40, 50, or can be offset from the central axis. Embodiments are also contemplated including multiples passages extending therealong. In still other embodiments, the passages open externally along the length of members 40, 50 and linking member 60 is secured to members 40, 50 by adhesives, fasteners or other suitable means.

In FIG. 4 there is shown another embodiment construct 122 having a first motion preserving member 40 and a second motion preserving member 140 adjacent outer end 44. Linking member 60 extends through motion preventing member 50 and motion preserving members 40, 140 to provide a link that couples the elongated bodies of members 40, 50 to one another. Motion preserving member 140 can be provided to extend the motion preserving segment 124 of construct 122 to one or more additional levels along the spinal column. The motion preventing segment 126 of construct 122 can be extended by one or more motion preventing members extending from outer end 54 of motion preventing member 50.

Figure 5:
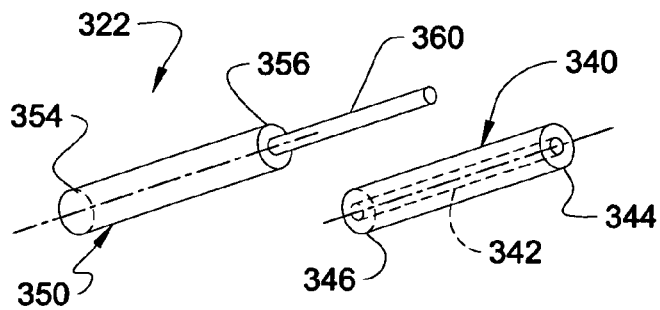
FIG. 5 is an exploded perspective view of another embodiment multi-level multi-functional stabilization construct.

In FIG. 5 there is shown another embodiment stabilization construct 322 including a motion preserving member 340 and a motion preventing member 350. Motion preserving member 340 includes an elongated body extending between an outer end 344 and an intermediate end 346. Passage 342 extends between ends 344, 346. Motion preventing member 350 includes an elongated body extending between an outer end 354 and an intermediate end 356. A linking member 360 extends from intermediate end 356, and is positionable in passage 342 of motion preserving member 340.

In the illustrated embodiment, linking member 360 includes a rigid body structure that is formed by a smaller size portion of motion preventing member 350. Linking member 360 is telescopingly received in and extends along a portion of the length of motion preserving member 340. Motion preserving member 340 can flex, bend and/or compress along linking member 360 to maintain motion capabilities of first vertebral level 11.

Figure 6:
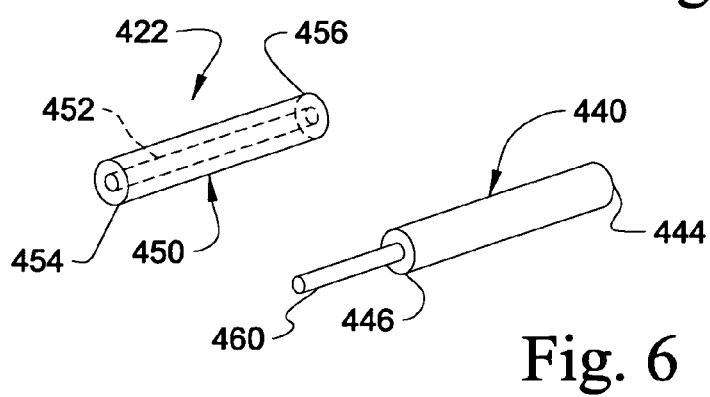
FIG. 6 is an exploded perspective view of another embodiment multi-level multi-functional stabilization construct.

In FIG. 6 there is shown another embodiment stabilization construct 422 including a motion preserving member 440 and a motion preventing member 450. Motion preserving member 440 includes an elongated body extending between an outer end 444 and an intermediate end 446. A linking member 460 extends from intermediate end 446 and is formed by a reduced size portion of motion preserving member 440. Motion preventing member 450 includes an elongated body extending between an outer end 454 and an intermediate end 456. A passage 452 extends through the body between ends 454, 456. Linking member 460 is positionable in passage 452 of motion preventing member 450.

In the illustrated embodiment, linking member 460 includes a body structure that is formed by a smaller sized portion of motion preserving member 440. Linking member 460 can be flexible and telescopingly received in passage 452 of motion preventing member 450 while maintaining the ability of motion preserving member 440 to flex, bend and/or compress in response to motion of the spinal column segment. In one embodiment, linking member 460 is integrally formed with motion preserving member 440.

Figure 8:
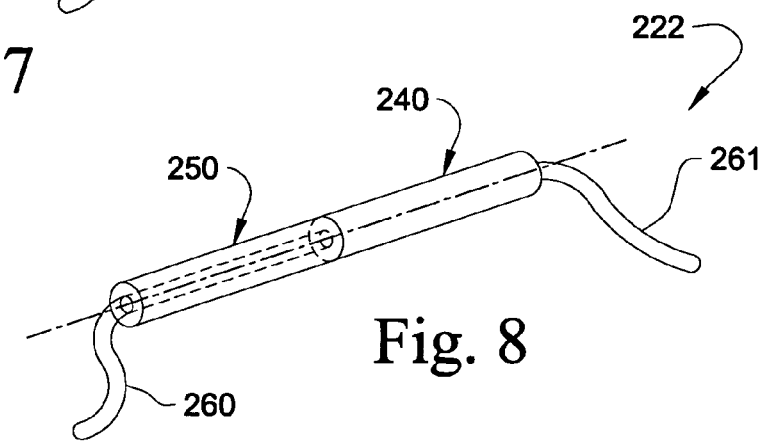
FIG. 8 is a perspective view of the construct of FIG. 7.

FIGS. 7 and 8 show another embodiment stabilization construct 222. Stabilization construct 222 includes a motion preserving member 240 and a motion preventing member 250. Motion preventing member 250 includes a passage 252 extending between an outer end 254 and an intermediate end 256. Motion preserving member 240 includes an elongated body extending between an outer end 244 and an intermediate end 246. A flexible linking member 260 extends from intermediate end 246. A second linking member portion 261 can extend from outer end 244 for engagement with a second motion preserving member (not shown). Linking member 260 is positionable in passage 252 and can be engaged to motion preventing member 250 to maintain members 240, 250 in end-to-end engagement with one another. The body of motion preserving member 240 can be over-molded or otherwise formed or engaged with linking member 260 (and portion 261 if so provided) so that linking member 260 is irremovably secured thereto.

Referring now to FIGS. 9-11, there are shown various end-to-end abutting engagement arrangements between adjacent ones of the motion preserving member and motion preventing member of the construct. The motion preserving and motion preventing members in FIGS. 9-11 can include any of the forms discussed herein, and may be coupled to one another with a linking member as discussed above. In FIGS. 9A and 9B, one of the members 540, 550 is a motion preserving member and the other of the members 540, 550 is a motion preventing member. Member 540 includes a concavely curved end 542 and member 550 includes a convexly curved end 552. Ends 542, 552 contact one another along longitudinal axis 548. The concave-convex curvature resists slippage of the members 540, 550 relative to one another, at least in one direction relative to axis 548, and maintains alignment of the adjacent members 540, 550.

In FIGS. 10A and 10B, one of the members 640, 650 is a motion preserving member and the other of the members 640, 650 is a motion preventing member. Member 640 includes a spherically curved end 642 and member 650 includes a spherically shaped recessed end 652. Ends 642, 652 contact one another along longitudinal axis 648. The concave-convex curvature resists slippage of the members 640, 650 relative to one another in all directions transversely to axis 648, maintaining alignment of the intermediate ends 642, 652 of the adjacent members 640, 650.

FIG. 11 shows a perspective view of another embodiment construct including a first member 740 and a second member 750. One of the members 740, 750 is a motion preserving member and the other of the members 740, 750 is a motion preventing member. Member 750 includes a non-circular end 752, and member 740 includes an end 742 with a correspondingly shaped recess. Ends 742, 752 non-rotatably engage one another to prevent the ends from slipping laterally relative to one another, and also to resist rotation of the members relative to one another.

FIGS. 12-15 include partial section views showing other connection arrangements of between motion preserving and motion preventing members of a stabilization construct. Only half the connection arrangement is shown, it being understood that the members and connection arrangement can be concentric and symmetrical about the longitudinal axis of the construct.

FIG. 12 is a partial section view of one embodiment connection arrangement between first and second members 840, 850 of a stabilization construct. Second member 850 includes an axial recess 852, and first member 840 includes an axial extension 842. Extension 842 is received in recess 852, and includes a shoulder 843 positionable in abutting engagement with an end wall 853 of second member 850.

FIG. 13 is a partial section view of another embodiment connection arrangement between first and second members 860, 865 of a stabilization construct. First member 860 includes an axial recess 862, and second member 865 includes an axial extension 866. Extension 866 is received in recess 862, and includes a tapered shoulder 867 positionable in abutting engagement with a tapered inner wall 863 of first member 860 extending about recess 862.

FIG. 14 is a partial section view of another embodiment connection arrangement between first and second members 870, 875 of a stabilization construct. First member 870 includes an axial recess 872, and second member 875 includes an axial extension 876. Extension 876 is received in recess 872, and includes an external circumferential groove 877 and adjacent shoulder 878. First member 870 includes a distal tooth 874 along an inner wall thereof projecting into recess 872 and a valley 873 adjacent tooth 874. Tooth 874 is received in groove 877, and shoulder 878 abuts shoulder 873. The interfitting engagement axially constrains first and second member 870, 875 relative to one another.

FIG. 15 is a partial section view of another embodiment connection arrangement between first and second members 880, 885 of a stabilization construct. First member 880 includes an axial recess 882, and second member 885 includes an axial extension 886. Extension 886 is received in recess 882, and extension 886 includes a tapered shoulder having a series of projections 888 extending therealong. First member 880 includes a series of valleys 884 extending along a tapered inner shoulder thereof. Valleys and projections 884, 888 are engageable to one another in interdigitating fashion to axially secure the members of the stabilization construct to one another. The projections can be in the form of concentric grooves and recesses, or threads to provide threaded engagement between the members 880, 885.

In FIG. 16, there is shown the members 870, 875 of FIG. 14 and a clamp 890. However, it should be understood that clamp 890 has application with any of the connection arrangement embodiments discussed herein. Joint clamp 890 includes first clamping member 892 and second clamping member 894 moveable relative to one another to apply a clamping force at the connection between members 870, 875. Clamp 890 can provide axial securement or increase the axial constraint provided by the connection arrangement between members of the construct.

In FIG. 17, there is shown the members 840, 850 of FIG. 12 and a crimp 900. However, it should be understood that crimp 900 has application with any of the connection arrangement embodiments discussed herein. Crimp 900 includes a circumferential body 904 and a passage 902 that receives the members 840, 850 therethrough. Body 904 is crimpable about the connection arrangement between members 840, 850 to provide axial securement or increase the axial constraint provided by the connection arrangement between members of the construct.

In FIG. 18, there is shown the members 840, 850 of FIG. 12 and a connector 910. However, it should be understood that connector 910 has application with any of the connection arrangement embodiments discussed herein. Connector 910 includes a body 916 extending between and connecting engaging members 912, 914 to one another. Engaging members 912, 914 engage respective ones of the members 840, 850, and secure the members 840, 850 to body 916. In one form, body 916 is a bracket that extends between engaging members 912, 914. In another form, body 916 is a body that extends about members 840, 850, and engaging members 912, 914 are set screws engageable in threaded passages of the body 916 into contact with the members 840, 850.

The motion preserving member and motion preventing member can be made from one or more materials that possesses the appropriate strength characteristics necessary to withstand loading from the human body and, depending on its function, either substantially preserves motion or substantially prevents motion. In addition, the materials are compatible with the human body. Materials include ceramics, plastics, metals, elastomers, shape memory materials, or carbon fiber composites. The linking member may be of any suitable form, such as a suture, wire, tether, band, cord, cable, rope, rod, link, or strut, for example. The linking member may also be made from any material compatible with the human body, including ceramics, plastics, metals, elastomers, shape memory material, or carbon fiber composites.

The above described alternative configurations for the constructs can have dimensions that will vary depending upon the specific design necessary for a specific patient. More particularly, the dimensions and geometric shapes can vary based on patient anatomy, physiology, and the type of material or materials used in the construct.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A multi-level, multi-functional spinal stabilization system, comprising:
  a construct positionable along at least first and second levels of a spinal column, said construct including a motion preserving portion and a motion preventing portion, said motion preserving portion including a first flexible, elongate body and said motion preventing portion including a second substantially rigid, elongate body and further comprising:
  a flexible linking member extending through passages of said first and second bodies to flexibly link said first and second bodies in end-to-end engagement with one another;
  a first anchor engageable to a first vertebra, a second anchor engageable to a second vertebrae and a third anchor engageable to a third vertebra with the first, second and third vertebrae comprising the first and second levels of the spinal column, wherein said first body includes a length adapted to extend from said first anchor across the first level of the spinal column toward said second anchor to said second body when said first and second anchors are engaged to the first and second vertebrae comprising the first level to preserve motion of the first level and said second body includes a length adapted to extend from said second anchor to said third anchor when said second and third anchors are engaged to the second and third vertebrae comprising the second level to prevent motion of the second level.

2. The system of claim 1, wherein said first and second bodies each include a longitudinal passage extending therethrough and said flexible linking member is positioned through said passages.

3. The system of claim 1, wherein said end-to-end engagement includes adjacent ends of said first and second bodies received in form fitting engagement with one another.

4. The system of claim 3, wherein one of said adjacent ends is spherically shaped and the other of said adjacent ends includes a spherical recess.

5. The system of claim 3, wherein one of said adjacent ends includes a non-circular shape and the other of said adjacent ends includes a correspondingly shaped recess to non-rotatably receive said non-circular end.

6. The system of claim 1, wherein said construct is structured for posterior engagement to the first and second vertebral levels at a location offset to a first side of a central axis of the spinal column, and further comprising a second construct substantially identical to said construct and structured for posterior engagement to the first and second vertebral levels at a location offset to a second side of the central axis of the spinal column.

7. The system of claim 6, further comprising at least one fusion implant positionable in a disc space of the second vertebral level.

8. The system of claim 1, wherein said motion preserving portion includes a third elongate body linked with said first elongate body at an end thereof opposite said second elongate body, wherein said third elongate body includes a length sized to extend between anchors engaged to the first vertebra and a fourth vertebra opposite the second vertebra.

9. A multi-level, multi-functional spinal stabilization system, comprising:
   a construct positionable along at least first and second levels of a spinal column, said construct including a motion preserving portion and a motion preventing portion, said motion preserving portion including a first flexible, elongate body and said motion preventing portion including a second substantially rigid, elongate body and further comprising:
   a flexible linking member extending through passages of said first and second bodies to flexibly link said first and second bodies in end-to-end engagement with one another; and
   a first anchor engageable to a first vertebra, a second anchor engageable to a second vertebrae and a third anchor engageable to a third vertebra with the first, second and third vertebrae comprising the first and second levels of the spinal column, wherein said first body includes a length adapted to extend from said first anchor across the first level of the spinal column toward said second anchor to said second body when said first and second anchors are engaged to the first and second vertebrae comprising the first level to preserve motion of the first level and said second body includes a length adapted to extend from said second anchor to said third anchor when said second and third anchors are engaged to the second and third vertebrae comprising the second level to prevent motion of the second level, wherein said first and second bodies each include a longitudinal passage extending therethrough and said flexible linking member is positioned through said passages and said first and second bodies are crimped into engagement with said linking member.

10. A multi-level, multi-functional spinal stabilization system, comprising:
    a first elongate body having a length sized for positioning between first and second anchors when said first and second anchors are engaged to respective ones of first and second vertebrae of a first vertebral level;
    a second elongate body having a length sized for positioning from said second anchor when said second anchor is engaged to the second vertebra to a third anchor when said third anchor is engaged to a third vertebra of a second vertebral level adjacent the first vertebral level, said second elongate body being rigid between said second and third anchors to prevent motion of the second vertebral level and said first body extending from said first anchor to said second elongate body and being flexible to permit motion of the first vertebral level; and
    a linking member extending between and flexibly linking the first and second bodies with one another in end-to-end engagement.

11. The system of claim 10, wherein said first and second bodies each include a longitudinal passage extending therethrough and said linking member is positioned through said passages.

12. The system of claim 10, wherein said first body includes a passage extending at least partially therethrough and said second body includes a linking member integrally formed therewith, said linking member being received in said passage of said first body.

13. The system of claim 10, wherein said first body includes a linking member extending therefrom and said second body includes a passage receiving said linking member therein.

14. The system of claim 10, wherein said end-to-end engagement includes adjacent ends of said first and second bodies received in form fitting engagement with one another.

15. The system of claim 14, wherein one of said adjacent ends includes a non-circular shape and the other of said adjacent ends includes a correspondingly shaped recess to non-rotatably receive said non-circular end.

16. The system of claim 14, wherein one of said adjacent ends includes an axial extension having a circumferential groove and the other of said ends includes a recess for receiving said extension and a circumferential tooth extending into said recess positionable in said groove.

17. The system of claim 14, wherein one of said adjacent ends includes an axial extension having a series of external circumferential projections and the other of said ends includes a recess for receiving said extension with an internal wall having a series of circumferential valleys in interdigitating engagement with said projections.

18. The system of claim 14, further comprising a member about said form fitting engagement engaged to each of said first and second members, said member selected from the group consisting of: a crimp, a clamp and a connector.

19. A method for stabilizing at least two levels of a spinal column segment, comprising:
    coupling a first elongate body to a second elongate body with a linking member extending between the first and second bodies;
    engaging the first elongate body to first and second vertebrae of a first vertebral level, said first body being flexible to permit motion of the first vertebral level; and
    engaging the second elongate body to the second vertebra and a third vertebra of a second vertebral level adjacent the first vertebral level, said second elongate body being rigid to prevent motion of the second vertebral level, wherein coupling the first and second elongate bodies includes positioning the first and second bodies in end-to-end engagement with one another.

20. The method of claim 19, further comprising:
    coupling a third elongate body to the first elongate body at an end thereof opposite the second elongate body with the linking member;
    engaging the third elongate body between the first vertebra and a fourth vertebra of a third vertebral level adjacent the first vertebral level, said third body being flexible to permit motion of the third vertebral level.

21. The method of claim 19, further comprising positioning a fusion device between the second and third vertebrae.

22. The method of claim 21, wherein the first and second elongate bodies form a construct posteriorly engaged to the first and second vertebral levels at a location offset to a first side of a central axis of the spinal column, and further comprising engaging a substantially identical second construct posteriorly to the first and second vertebral levels at a location offset to a second side of the central axis of the spinal column.

23. The method of claim 19, wherein said wherein said first and second bodies each include a longitudinal passage extending therethrough and said flexible linking member is positioned through said passages.

24. A multi-level, multi-functional spinal stabilization system, comprising:
    a construct positionable along at least first and second levels of a spinal column, said construct including:

a motion preserving portion including a first flexible, elongate body extending between an outer end and an opposite intermediate end, said motion preserving portion further including a flexible linking member extending from said intermediate end with said linking member being formed by a reduced size portion of said first body;

a motion preventing portion including a second rigid, elongate body extending between an outer end and an intermediate end of said second body, said second body further including a passage opening at said intermediate end thereof and said linking member is received in said passage to flexibly link said first and second bodies in end-to-end engagement with one another; and a first anchor engageable to a first vertebra, a second anchor engageable to a second vertebrae and a third anchor engageable to a third vertebra with the first, second and third vertebrae comprising the first and second levels of the spinal column, wherein said first body includes a length adapted to extend from said first anchor across the first level of the spinal column toward said second anchor to said second body when said first and second anchors are engaged to the first and second vertebrae comprising the first level to preserve motion of the first level and said second body includes a length adapted to extend from said second anchor to said third anchor when said second and third anchors are engaged to the second and third vertebrae comprising the second level to prevent motion of the second level.

25. The system of claim 24, wherein said linking member also extends from said first end of said first body of said motion preserving portion.

26. A multi-level, multi-functional spinal stabilization system, comprising:

a construct positionable along at least first and second levels of a spinal column, said construct including:

a motion preserving portion including a first flexible, elongate body extending between an outer end and an opposite intermediate end, said motion preserving portion further including a passage extending therethrough opening at said intermediate end;

a motion preventing portion including a second substantially rigid, elongate body extending between an outer end and an intermediate end of said second body, said second body further including a rigid linking member extending from said intermediate end with said linking member being formed by a reduced size portion of said second body, said linking member being received in said passage of said first body to link said first and second bodies in end-to-end engagement with one another; and a first anchor engageable to a first vertebra, a second anchor engageable to a second vertebrae and a third anchor engageable to a third vertebra with the first, second and third vertebrae comprising the first and second levels of the spinal column, wherein said first body includes a length adapted to extend from said first anchor across the first level of the spinal column toward said second anchor to said second body when said first and second anchors are engaged to the first and second vertebrae comprising the first level to preserve motion of the first level and said second body includes a length adapted to extend from said second anchor to said third anchor when said second and third anchors are engaged to the second and third vertebrae comprising the second level to prevent motion of the second level.

* * * * *